US00PP29360P2

(12) United States Plant Patent
van Langen

(10) Patent No.: US PP29,360 P2
(45) Date of Patent: Jun. 5, 2018

(54) ***ECHEVERIA×PACHYPHYTUM* PLANT NAMED 'ASANTE SANA'**

(50) Latin Name: *Echeveria lilacina×Pachyphytum oviferum*
Varietal Denomination: Asante Sana

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days. days.

(21) Appl. No.: 15/530,487

(22) Filed: Jan. 20, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Samuel R. McCoy, Jr.

(57) ABSTRACT

A new and distinct *Echeveria×Pachyphytum* cultivar named 'Asante Sana' which is characterized by large, thick foliage with a slight upwardly curved attitude, arranged in a compact rosette. The obovate to broad oblanceolate foliage is heavily pruinose and exhibits a white coloration with a soft blue hue. The new variety has shown to be uniform and stable in the resulting generations from asexual propagation.

4 Drawing Sheets

Latin name of the genus and species: The Latin name of the genus and species of the novel variety disclosed herein is *Echeveria lilacina×Pachyphytum oviferum* hybrid.

Variety denomination: The inventive variety of *Echeveria×Pachyphytum* disclosed herein has been given the variety denomination 'Asante Sana'.

BACKGROUND OF THE INVENTION

Parentage: 'Asante Sana' is the result of a planned breeding program carried out at a commercial greenhouse in Heerhugowaard, the Netherlands. In the spring of 2011, the inventor performed the controlled intergeneric cross-pollination of the species *Echeveria lilacina* (unnamed), the seed parent, with the species *Pachyphytum oviferum* (unnamed), the pollen parent. In the summer of 2012, a seedling that exhibited potential commercial value was selected from all other progeny of the same cross. The seedling was given the reference code "13-0010" and allowed to grow to a mature size, for further evaluation to confirm the stability of the characteristics initially observed. In the summer of 2013, the claimed plant was selected for commercialized.

Asexual Reproduction: Asexual reproduction of the new cultivar 'Asante Sana', by way of rooting leaf cuttings, was first initiated in the spring of 2014 at the inventor's commercial greenhouse in Heerhugowaard, the Netherlands. Through six subsequent generations, the unique features of this cultivar have proven to be stable and true to type.

SUMMARY OF THE INVENTION

The cultivar 'Asante Sana' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Asante Sana'. These characteristics in combination distinguish 'Asante Sana' as a new and distinct *Echeveria×Pachyphytum* cultivar:

1. 'Asante Sana' exhibits large, thick foliage with a slight upwardly curved attitude, arranged in a compact rosette; and
2. 'Asante Sana' exhibits obovate to broad oblanceolate foliage with an apiculate apex; and
3. 'Asante Sana' exhibits heavily pruinose foliage which gives the foliage a white coloration with a soft blue hue.

BOTANICAL DESCRIPTION OF THE PLANT

Figure 1:
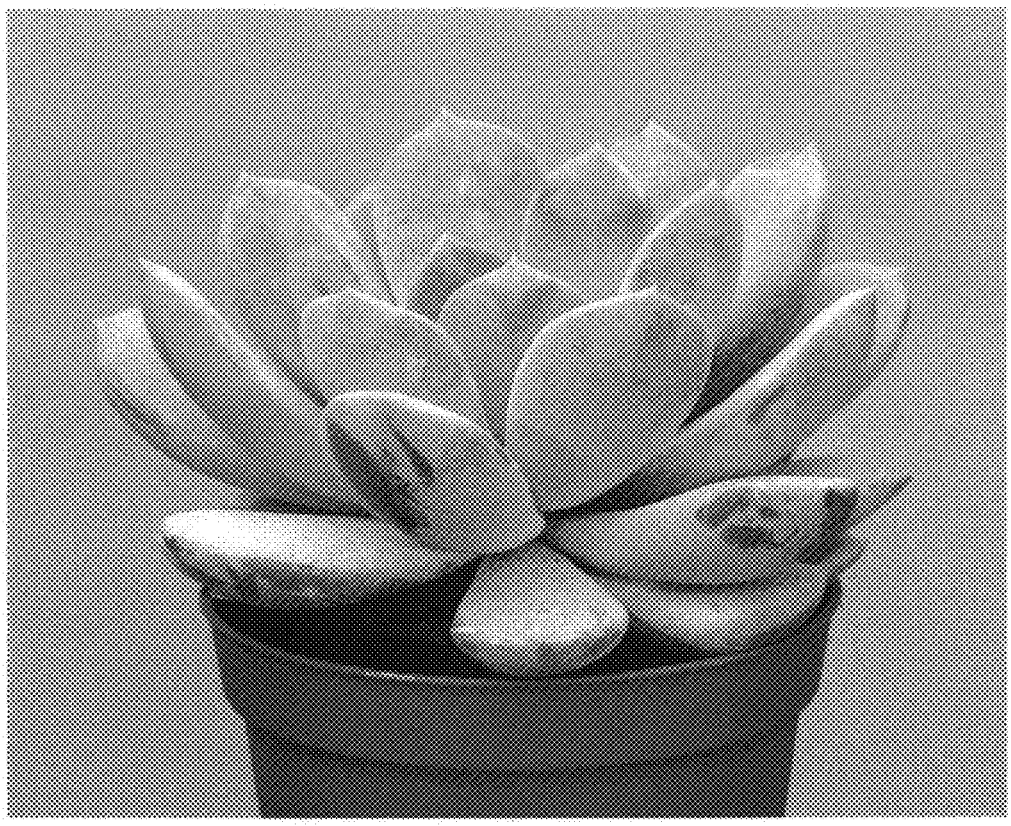
FIG. 1 illustrates, as nearly true as it is reasonably possible to make the same in color photographs of this type, an exemplary plant of 'Asante Sana' grown in a commercial greenhouse in Heerhugowaard, the Netherlands. This plant is approximately 9 months old, shown planted in an 8.5 cm container.
Figure 2:
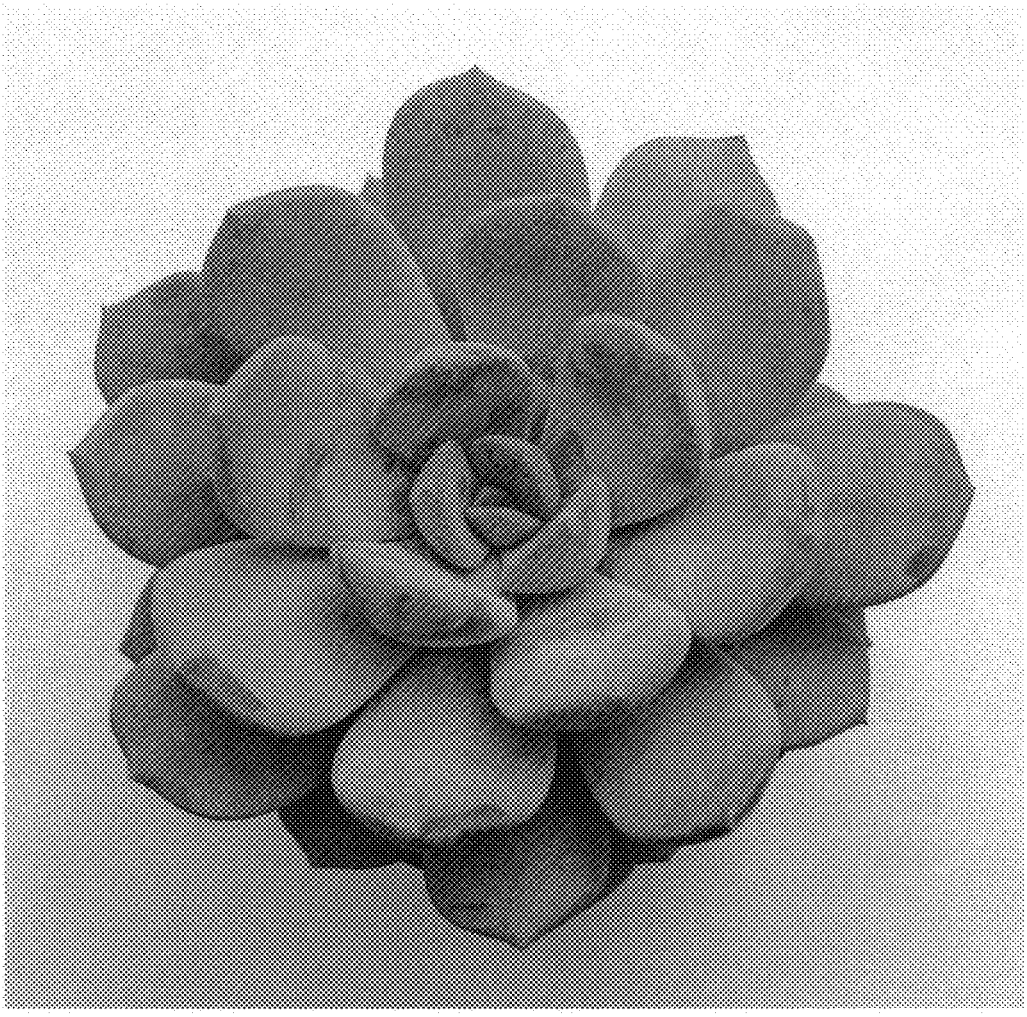
FIG. 2 illustrates, as nearly true as it is reasonably possible to make the same in color photographs of this type, the typical foliage arrangement of 'Asante Sana'.
Figure 3:
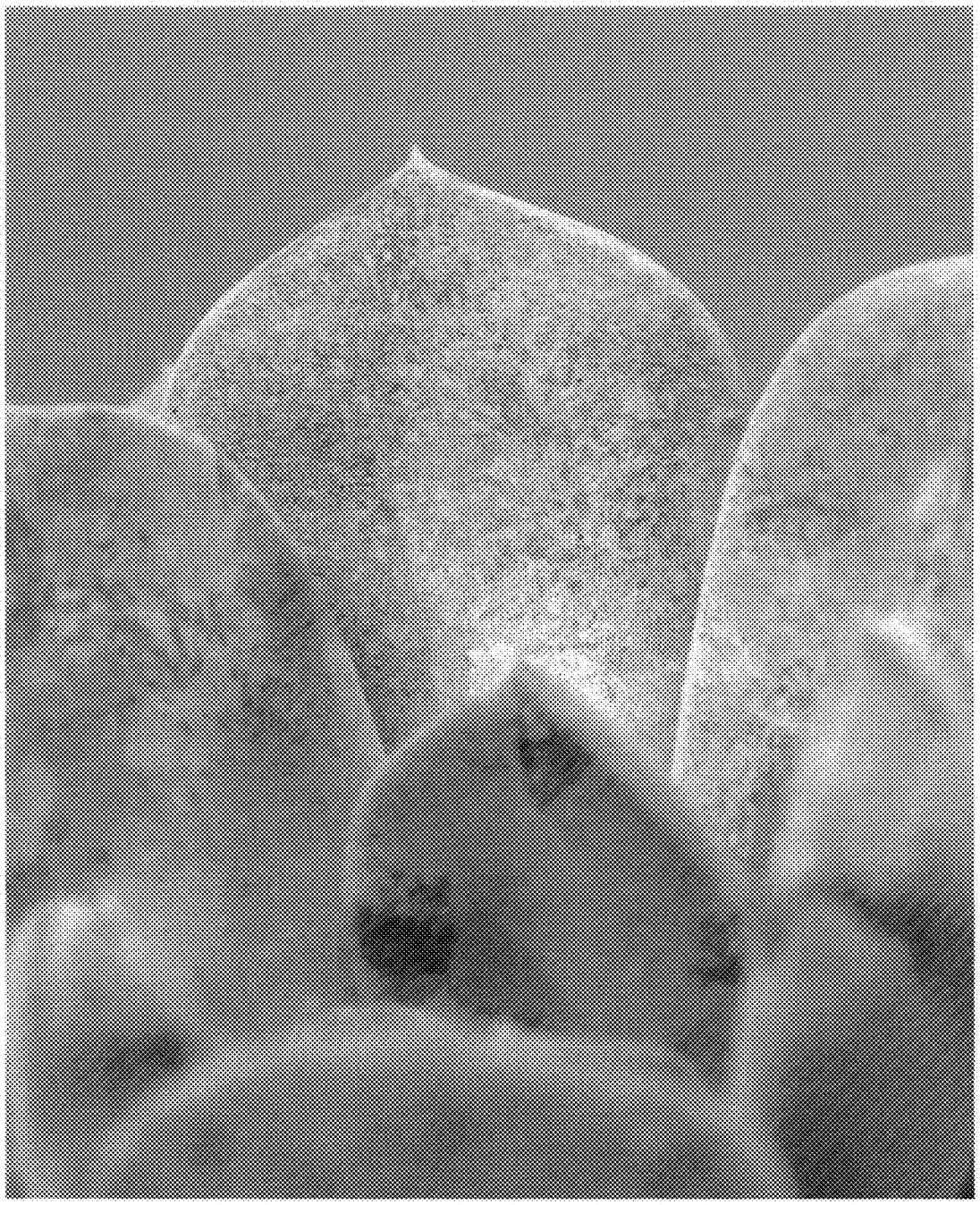
FIG. 3 illustrates, as nearly true as it is reasonably possible to make the same in color photographs of this type, the adaxial surface of the mature foliage 'Asante Sana'.
Figure 4:
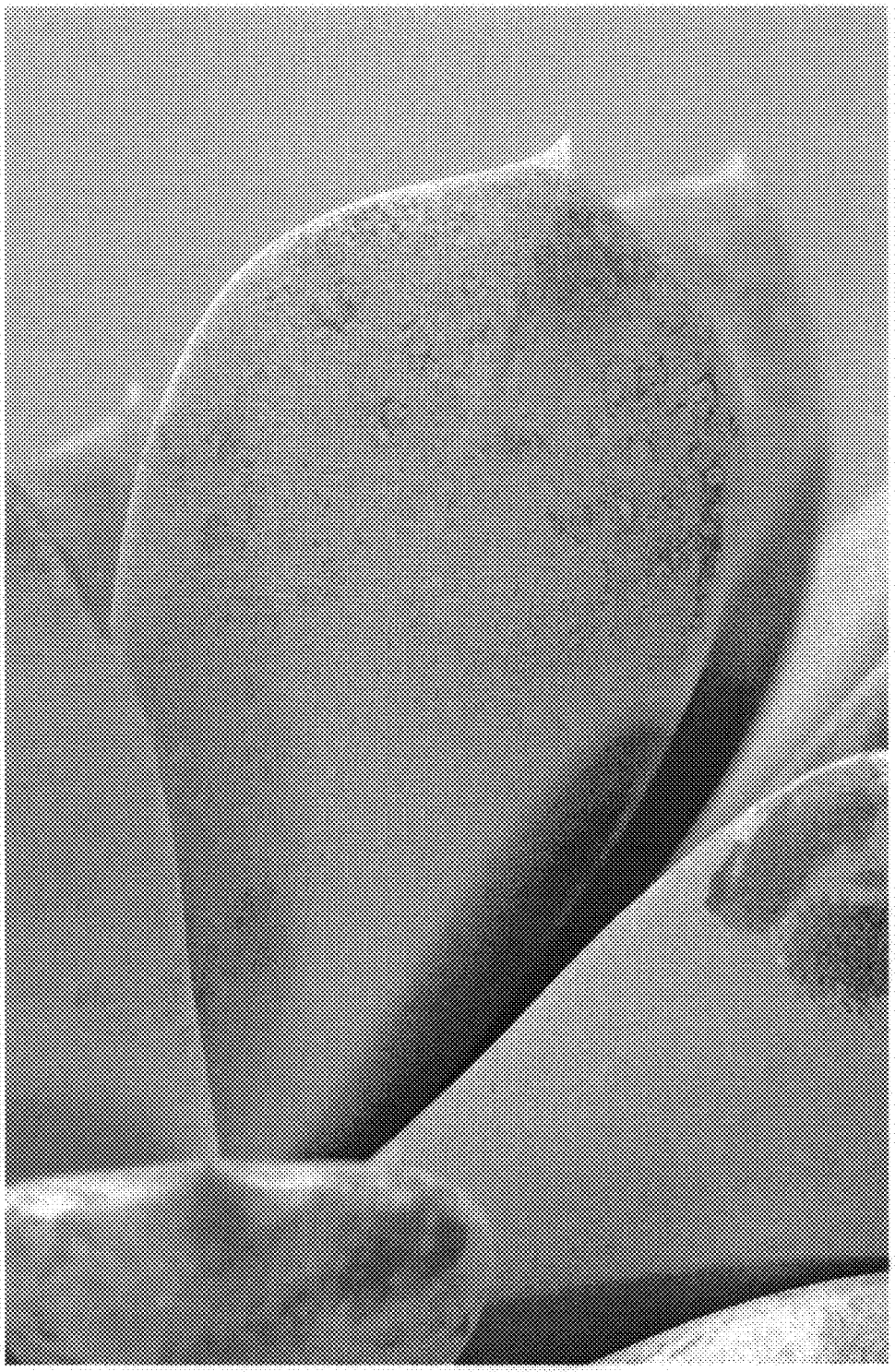
FIG. 4 illustrates, as nearly true as it is reasonably possible to make the same in color photographs of this type, the abaxial surface of the mature foliage 'Asante Sana'.

The following observations and measurements made in November of 2016 describe averages from a sample set of six specimens of 9 months old 'Asante Sana' plants grown in 8.5 cm nursery containers at commercial greenhouse in Heerhugowaard, the Netherlands. Plants were produced using conventional greenhouse production protocols for *Echeveria* which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'Asante Sana' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'Asante Sana' and a comparison with the parents is provided below.

Plant description:

*Growth habit*.—Succulent perennial with foliage growing in a non-branched basal rosette.

*Plant shape*.—Flattened globular.

*Height from soil level to top of foliar plane*.—7.2 cm.

*Plant spread*.—Average of 11.3 cm.

*Growth rate*.—Low.

*Plant vigor*.—Low.

*Propagation*.—Type — Leaf cuttings. Time to initiate rooting — Approximately 21 to 35 days at approximately 18 degrees Celsius. Crop time — Approximately 18 to 22 weeks to produce a marketable plant in a 7 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 32 leaves per rosette.

*Shape*.—Thick, succulent leaves which are obovate to broad oblanceolate.

*Dimensions*.—5.7 cm long, 2.5 cm wide, and 1.0 cm thick, on average.

*Aspect*.—Flat.

*Attitude*.—Very slightly curved upward.

*Apex*.—Short apiculate.

*Base*.—Cuneate.

*Margin*.—Entire; not undulated or lobed.

*Pubescence, texture and luster of the adaxial surface*.—Glabrous, smooth, and matte; moderately pruinose, colored in between blue-green, nearest to RHS 115D, and greyed-green, nearest to RHS 188D.

*Pubescence, texture and luster of the abaxial surface*.—Glabrous, smooth, and matte; moderately pruinose, colored in between blue-green, nearest to RHS 115D, and greyed-green, nearest to RHS 188D.

*Color*.—Juvenile foliage, adaxial surface — Greyed-green, nearest to RHS 194A, and fading to white towards the base, nearest to RHS 155B. Juvenile foliage, abaxial surface — Greyed-green, nearest to RHS 194A; slightly more greyed towards the apex, nearest to RHS 195A; fading to white towards the base, nearest to RHS 155C. Mature foliage, adaxial surface — Greyed-green, in between RHS 194A and 195A, and fading more greenish towards the base, near RHS 194A, and ultimately fading to green-white at the base, nearest to RHS 157D. Mature foliage, abaxial surface — Greyed-green, nearest to RHS 194A; fading more greyish towards the apex, near RHS 195A; fading to green-white towards the base, nearest to RHS 157D.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'Asante Sana' differ from the seed parent, *Echeveria lilacina*, which is also the closest known comparator, in the following characteristics described in Table 1 below.

TABLE 1

| Characteristic | 'Asante Sana' | *Echeveria lilacina* |
|---|---|---|
| Leaf apex. | Short apiculate. | Acuminate. |
| Leaf thickness. | Thicker than the parent. | Thinner than 'Asante Sana'. |
| General coloration of the mature foliage. | White with a soft blue hue. | White with a lilac hue. |

Plants of the new cultivar 'Asante Sana' differ from the pollen parent, *Pachyphytum oviferum*, which is also the closest known comparator, in the following characteristics described in Table 2 below.

TABLE 2

| Characteristic | 'Asante Sana' | *Pachiphytum oviferum* |
|---|---|---|
| Leaf size. | Larger than the parent. | Smaller than 'Asante Sana'. |
| Leaf thickness. | Thicker than the parent. | Thinner than 'Asante Sana'. |
| Leaf apex. | Short apiculate. | Rounded. |
| General coloration of the mature foliage. | White with a soft blue hue. | Greyed-white. |

That which is claimed is:

1. A new and distinct variety of *Echeveria*×*Pachyphytum* plant named 'Asante Sana', substantially as described and illustrated herein.

* * * * *